(12) United States Patent
Natan et al.

(10) Patent No.: US 7,045,049 B1
(45) Date of Patent: May 16, 2006

(54) METHOD OF MANUFACTURE OF COLLOIDAL ROD PARTICLES AS NANOBAR CODES

(75) Inventors: Michael J. Natan, Los Altos, CA (US); Thomas E. Mallouk, State College, PA (US); Benjamin R. Martin, State College, PA (US); Brian D. Reiss, State College, PA (US); Louis J. Dietz, Mountain View, CA (US); James L. Winkler, Sunnyvale, CA (US)

(73) Assignee: Nanoplex Technologies, Inc., Menlo Park, CA (US)

( * ) Notice: Subject to any disclaimer, the term of this patent is extended or adjusted under 35 U.S.C. 154(b) by 213 days.

(21) Appl. No.: 09/677,203

(22) Filed: Oct. 2, 2000

Related U.S. Application Data

(63) Continuation-in-part of application No. 09/598,395, filed on Jun. 20, 2000.
(60) Provisional application No. 60/212,167, filed on Jun. 16, 2000, provisional application No. 60/194,616, filed on Apr. 5, 2000, provisional application No. 60/190,247, filed on Mar. 17, 2000, provisional application No. 60/189,151, filed on Mar. 14, 2000, and provisional application No. 60/157,326, filed on Oct. 1, 1999.

(51) Int. Cl.
C25D 5/02 (2006.01)

(52) U.S. Cl. ...................................... 205/118; 205/122
(58) Field of Classification Search ................. 205/122, 205/118; 427/468, 123, 126.1, 126.3, 126.4, 427/126.5, 126.6
See application file for complete search history.

(56) References Cited

U.S. PATENT DOCUMENTS

| 3,755,730 A | 8/1973 | Vogelgesang |
| 3,878,367 A | 4/1975 | Fayling et al. |
| 3,897,284 A | 7/1975 | Livesay |

(Continued)

FOREIGN PATENT DOCUMENTS

| EP | 0602829 | * | 6/1994 |
| EP | WO 99/47253 | * | 9/1999 |
| EP | 1018365 | | 7/2000 |
| WO | WO 97/15390 | | 5/1997 |
| WO | WO 99/18240 | | 4/1999 |
| WO | WO 94/41006 | | 8/1999 |
| WO | WO 99/64580 | * | 12/1999 |
| WO | WO 00/01475 | | 1/2000 |
| WO | WO 00/63419 | | 10/2000 |
| WO | WO 00/63695 | | 10/2000 |
| WO | WO 01/25002 | * | 4/2001 |
| WO | WO 01/26038 | * | 4/2001 |

OTHER PUBLICATIONS

AlMawlawi et al. (1991) J. Appl. Phys. 70(8): 4421–4425.
Al–Rawashdeh et al. (1998) J. Phys. Chem. 13 102:361–371.
Braun et al., Nature 402 (1999) 603.
Brumlik et al., J. Am. Chem. Soc. 113 (1991) 3174.
Foss et al. (1992) J. Phys. Chem. 96:9001–9007.
Foss et al., J. Phys. Chem. 98 (1994) 2963.
Hornyak et al. (1997) J. Phys. Chem. 101:1548–1555.
Hulteen et al., J. Mater. Chem. 7 (1997) 1075.
Jirage et al. (1997) Science 278:655–658.
Martin (1995) Acc. Chem. Res. 28:61–68.
Nishizawa et al. (1995) Science 268:700–702.
Penner et al. (1987) Anal. Chem. 59:2625–2630.

(Continued)

*Primary Examiner*—Arun S. Phasge
(74) *Attorney, Agent, or Firm*—Swanson & Bratschun L.L.C.; William Leschensky

(57) ABSTRACT

Synthetic methods for the manufacture of segmented nanoparticles are described.

25 Claims, 2 Drawing Sheets

U.S. PATENT DOCUMENTS

| | | | |
|---|---|---|---|
| 4,053,433 A | 10/1977 | Lee | |
| 4,098,935 A | 7/1978 | Knudsen | |
| 4,131,064 A | 12/1978 | Ryan et al. | 102/293 |
| 4,306,993 A | 12/1981 | Danielson et al. | |
| 4,329,393 A | 5/1982 | LaPerre et al. | |
| 4,390,452 A | 6/1983 | Stevens | |
| 4,397,142 A | 8/1983 | Bingham | |
| 4,469,623 A | 9/1984 | Danielson et al. | |
| 4,527,383 A | 7/1985 | Bingham | |
| 4,679,939 A | 7/1987 | Curry et al. | 356/336 |
| 4,855,930 A | 8/1989 | Chao et al. | 407/32 |
| 4,884,886 A | 12/1989 | Salzman et al. | 351/357 |
| 5,091,188 A | 2/1992 | Haynes | 424/450 |
| 5,303,710 A | 4/1994 | Bashkansky et al. | 600/476 |
| 5,449,565 A | 9/1995 | Aoki et al. | 428/694 |
| 5,508,164 A | 4/1996 | Kausch et al. | 435/6 |
| 5,512,131 A | 4/1996 | Kumar et al. | 438/738 |
| 5,547,748 A * | 8/1996 | Ruoff et al. | 423/439 |
| 5,547,849 A | 8/1996 | Baer et al. | |
| 5,556,764 A | 9/1996 | Sizto et al. | |
| 5,571,726 A | 11/1996 | Brooks et al. | |
| 5,599,615 A | 2/1997 | Swift et al. | |
| 5,645,619 A | 7/1997 | Erickson et al. | 51/309 |
| 5,667,667 A | 9/1997 | Southern | 205/687 |
| 5,674,743 A | 10/1997 | Ulmer | 435/257.2 |
| 5,732,150 A | 3/1998 | Zhou et al. | |
| 5,846,517 A | 12/1998 | Unger | 424/9.52 |
| 5,859,700 A | 1/1999 | Yang | |
| 5,927,621 A | 7/1999 | Ziolo et al. | 241/21 |
| 5,985,356 A | 11/1999 | Schultz et al. | 427/8 |
| 5,997,958 A * | 12/1999 | Sato et al. | 427/468 |
| 6,020,419 A * | 2/2000 | Bock et al. | 523/318 |
| 6,071,336 A | 6/2000 | Fairchild et al. | 106/464 |
| 6,093,302 A * | 7/2000 | Montgomery | 205/122 |
| 6,132,278 A | 10/2000 | Kang et al. | |
| 6,143,211 A * | 11/2000 | Mathiowitz et al. | 264/4 |
| 6,162,532 A * | 12/2000 | Black et al. | 427/128 |
| 6,172,902 B1 | 1/2001 | Wegrowe et al. | |
| 6,334,856 B1 | 1/2002 | Allen et al. | 604/191 |

OTHER PUBLICATIONS

Sandrock et al. (1999) J. Phys. Chem. B 103:11398–11406.
Tiernay et al. (1989) J. Phys. Chem. 93:2878–2880.
Liu et al. (1995) Physical Review B. 51(11) 7381–7384.
Piraux et al. (1999) J. Mater. Res. 14(7):3042–3050.
Schwarcher (1999) Electrochemical Society Interface. 20–24.
Cepak et al. (1997) Chem. Mater. 9:1065.
Cepak and Martin (1998) J. Phys. Chem. B 102:9985.
Davis et al. (1998) Chem. Mater. 10:2516.
El–Kouedi et al. (1998) Chem. Mater. 10:3287.
El_Kouedi and Foss. Jr. (2000) J. Phys. Chem. B. 104:4031.
Martin et al. (1990) J. Am. Chem. Soc. 112:8976.
Martin et al. (1999) Adv. Materials 11:1021.
Martin (1996) Chem. Mater. 8:1739.
McDade and Fulton (1997) Medical Device and Diagnostic Industry 19:75.
Meng et al. (1998) Solid State Communications 106:215.
Merchant and Weinberger (2000) Electrophoresis 2000 21:1164..
Michael et al. (1998) Anal. Chem. 70:1242.
Piatek et al. (1998) Nature Biotechnology 16:359.
van der Zande et al. (1997) J. Phys. Chem. B. 101:852.
Wang et al. (1996) Thin Solid Films 288:86.
Wong et al. (1996) Chem. Mater. 8:2041.
Zhang et al. (1999) Chem. Mater. 11:1659.
U.S. patent application Ser. No. 09/598,395, Natan et al., filed Jun. 20, 2000.
U.S. patent application Ser. No. 09/677,198, Natan et al., filed Oct. 2, 2000.
U.S. patent application Ser. No. 09/676,890, Natan et al., filed Oct. 2, 2000.
Al–Mawlawi et al. (1994) J. Mater. Res. 9:1014.
Bruchez et al. (1998) Science 281:2013.
Cepak and Martin (1999) Chem. Mater. 11:1363.
Piraux et al. (1994) Applied Physics Letters 65:2484–2486.
Blondel et al. (1994) Applied Physics Letters 65:3019–3021.
Dermody, et al., Abstracts of Paper American Chemical Society, 1999, 217 (1–2): pANYL 137.
Reiss, et al., Abstracts Of Paper Of The American Chemical Society, 1998, 216, P137–COLL.
Routkcvitch et al., J. Phys. Chem., 1996, 100(33):14037–47.
Sapp, et al., Chem. Mater., 1999, 11:1183–85.
Martin, et al., Adv. Mater. 11:1021–25 (Aug. 18, 1999).
Lehninger (1970) Biochemistry p. 640, The Molecular Basis of Cell Structure and Function, no month.
Dietz et al. (1996) Cytometry 23:177–186, no month.
Savas et al. (1996) J. Vac. Sci. Tech B 14:4167, no month.
Reiss, et al. (1998)72nd Colloid and Surface Science Symposium, American Chemical Society, University Park, PA, no month.
Savas et al. (1999) J. Applied Physics 85:6160, no month.
Mallouk et al. (2000)Abstract of Papers—American Chemical Society V220,PU440–U440, no month.
Mbdinyo et al. (2000) Abstracts of Papers—American Chemical Society V220, IEC–187, no month.
Reiss et al. (2000) Abstracts of Papers—American Chemical Society V220, PHYS–572, no month.
Natan et al. (2000)Presentation at CHI's 4th Annual Advances in Labels, Signals and Detection, no month.
Keating et al. (2000) Presentation at Electrochem' 2000, no month.
Keating et al. (2000) Abstracts of Papers—American Chemical Society V220, PU429–U429, no month.
Decker et al. (Nov. 1997) Journal of Vacuum Science and Technology: Part B 15(6):1949–1953.*
Nakajima et al. (Dec. 1994) Japanese Journal of Applied Physics 33(12B):L1796–L1798.*

* cited by examiner

US 7,045,049 B1

METHOD OF MANUFACTURE OF COLLOIDAL ROD PARTICLES AS NANOBAR CODES

RELATED APPLICATIONS

This application is a Continuation-in-Part of U.S. Utility application Ser. No. 09/598,395, filed Jun. 20, 2000, entitled "Colloidal Rod Particles as Nanobar Codes." The 09/598, 395 Application was Filed claiming the benefit of the filing date of U.S. Provisional Application Ser. No. 60/157,326, filed Oct. 1, 1999, entitled "Self Bar-coded Colloidal Metal Nanoparticles"; U.S. Provisional Application Ser. No. 60/189,151, filed Mar. 14, 2000, entitled "Nanoscale Barcodes"; U.S. Provisional Application Ser. No. 60/190,247, filed Mar. 17, 2000, entitled "Colloidal Rod Particles as Barcodes"; and U.S. Provisional Application Ser. No. 60/194,616, filed Apr. 5, 2000, entitled "Nanobarcodes: Technology Platform for Phenotyping." This application also claims the benefit of the filing date of U.S. Provisional Application Ser. No. 60/212,167, filed Jun. 16, 2000, entitled "Techniques for Multiple Parallel Nanobarcode Synthesis."

GOVERMENT LICENCE RIGHTS

The U.S. Goverment has a paid-up license in this invention and the right in limited circumstances to require the patent owner to license others on reasonable terms as provided for by the terms of N00014-98-1-0846 awarded by DARPA and ONR.

FIELD OF THE INVENTION

The present invention is directed to methods of manufacture of nanoparticles and approaches for such manufacture. In certain preferred embodiments of the invention, the nanoparticles may be used to encode information and thereby serve as molecular (or cellular) tags, labels and substrates.

BACKGROUND OF THE INVENTION

The present invention relates to methods of manufacture of segmented particles and assemblies of differentiable particles (which may or may not be segmented). Without a doubt, there has been a paradigm change in what is traditionally defined as bioanalytical chemistry. A major focus of these new technologies is to generate what could be called "increased per volume information content". This term encompasses several approaches, from reduction in the volume of sample required to carry out an assay, to highly parallel measurements ("multiplexing"), such as those involving immobilized molecular arrays, to incorporation of second (or third) information channels, such as in 2-D gel electrophoresis or CE-electrospray MS/MS.

Unfortunately, many of these seemingly revolutionary technologies are limited by a reliance on relatively pedestrian materials, methods, and analyses. For example, development of DNA microarrays ("gene chips") for analysis of gene expression and genotyping by Affymetrix, Incyte and similar companies has generated the wherewithal to immobilize up to 20,000 different fragments or full-length pieces of DNA in a spatially-defined 1-$cm^2$ array. At the same time, however, the use of these chips in all cases requires hybridization of DNA in solution to DNA immobilized on a planar surface, which is marked both by a decrease in the efficiency of hybridization (especially for cDNA) and a far greater degree of non-specific binding. It is unclear whether these problems can be completely overcome. Moreover, there is a general sense of disillusionment both about the cost of acquiring external technology and the lead-time required to develop DNA arraying internally.

A second example of how groundbreaking can be slowed by inferior tools is in pharmaceutical discovery by combinatorial chemistry. At the moment, solution phase, 5–10 μm diameter latex beads are used extensively as sites for molecular immobilization. Exploiting the widely adopted "split and pool" strategy, libraries of upwards of 100,000 compounds can be simply and rapidly generated. As a result, the bottleneck in drug discovery has shifted from synthesis to screening, and equally importantly, to compound identification, (i.e., which compound is on which bead?). Current approaches to the latter comprise "bead encoding", whereby each synthetic step applied to a bead is recorded by parallel addition of an organic "code" molecule; reading the code allows the identity of the drug lead on the bead to be identified. Unfortunately, the "code reading" protocols are far from optimal: in most every strategy, the code molecule must be cleaved from the bead and separately analyzed by HPLC, mass spectrometry or other methods. In other words, there is at present no way to identify potentially interesting drug candidates by direct, rapid interrogation of the beads on which they reside, even though there are numerous screening protocols in which such a capability would be desirable.

Two alternative technologies with potential relevance both to combinatorial chemistry and genetic analysis involve "self-encoded beads", in which a spectrally identifiable bead substitutes for a spatially defined position. In the approach pioneered by walt and co-workers, beads are chemically modified with a ratio of fluorescent dyes intended to uniquely identify the beads, which are then further modified with a unique chemistry (e.g. a different antibody or enzyme). The beads are then randomly dispersed on an etched fiber array so that one bead associates with each fiber. The identity of the bead is ascertained by its fluorescence readout, and the analyte is detected by fluorescence readout at the same fiber in a different spectral region. The seminal paper (Michael et al., Anal. Chem. 70, 1242–1248 (1998)) on this topic points out that with 6 different dyes (15 combinations of pairs) and with 10 different ratios of dyes, 150 "unique optical signatures" could be generated, each representing a different bead "flavor". A very similar strategy is described by workers at Luminex, who combine flavored beads ready for chemical modification (100 commercially available) with a flow cytometry-like analysis. (See, e.g., McDade et al., Med. Rev. Diag. Indust. 19, 75–82 (1997)). Once again, the particle flavor is determined by fluorescence, and once the biochemistry is put onto the bead, any spectrally distinct fluorescence generated due to the presence of analyte can be read out. Note that as currently configured, it is necessary to use one color of laser to interrogate the particle flavor, and another, separate laser to excite the bioassay fluorophores.

A more significant concern with self-encoded latex beads is the limitations imposed by the wide bandwidth associated with molecular fluorescence. If the frequency space of molecular fluorescence is used both for encoding and for bioassay analysis, it is hard to imagine how, for example, up to 20,000 different flavors could be generated. This problem might be alleviated somewhat by the use of combinations of glass-coated quantum dots, which exhibit narrower fluorescence bandwidths. (See, e.g. Bruchez et al., Science, 281, 2013–2016 (1998)). However, these "designer" nanoparticles arc quite difficult to prepare, and at the moment, there exist more types of fluorophores than (published) quantum dots. If, however, it were possible to generate very large numbers of intrinsically-differentiable particles by some means, then particle-based bioanalysis would become exceptionally attractive, insofar as a single technology platform could then be considered for the multiple high-information content research areas; including combinatorial chemistry, genomics, and proteomics (via multiplexed immunoassays).

Previous work has originally taught how metal can be deposited into the pores of a metallized membrane to make an array of metal nanoparticles embedded in the host. Their focus was on the optical and/or electrochemical properties of these materials. A similar technique was used to make segmented cylindrical magnetic nanoparticles in a host membrane, where the composition of the particles was varied along the length. In no case, however, have freestanding, rod-shaped nanoparticles with variable compositions along their length been prepared. Indeed, "freestanding" rod-shaped metal nanoparticles of a single composition, in which the length is at least one micron, have never been reported. Likewise, freestanding rod-shaped metal nanoparticles not embedded or otherwise contained within such host materials have never been reported. See, Martin et a., Adv. Materials 11 1021–25 (1999).

SUMMARY OF THE INVENTION

Rod-shaped nanoparticles have been prepared whose composition is varied along the length of the rod. These particles are referred to as nanoparticles or nanobar codes, though in reality some or all dimensions may be in the micron size range. The present invention is directed to methods of manufacture of such nanoparticles.

The present invention includes methods of manufacture of freestanding particles comprising a plurality of segment, wherein the particle length is from 10 nm to 50 μm and particle width is from 5 nm to 50 μm. The segments of the particles of the present invention may be comprised of any material. Included among the possible materials are a metal, any metal chalcogenide, a metal oxide, a metal sulfide, a metal selenide, a metal telluride, a metal alloy, a icital nitride, a metal phosphide, a metal antimonide, a semiconductor, a semi-metal, any organic compound or material, any inorganic compound or material, a particulate layer of material or a composite material. The segments of the particles of the present invention may be comprised of polymeric materials, crystalline or non-crystalline materials, amorphous materials or glasses. In certain preferred embodiments of the invention, the particles are "functionalized" (e.g., have their surface coated with IgG antibody). Commonly, such functionalization may be attached on selected or all segments, on the body or one or both lips of the particle. The functionalization may actually coat segments or the entire particle. Such functionalization may include organic compounds, such as an antibody, an antibody fragment or an oligonucleotide, inorganic compounds, and combinations thereof. Such functionalization may also be a detectable tag or comprise a species that will bind a detectable tag.

Also included within the present invention are methods of manufacture of an assembly or collection of particles comprising a plurality of types of particles, wherein each particle is from 20 nm to 50 μm in length and is comprised of a plurality of segments, and wherein the types of particles are differentiable. In the preferred embodiments, the particle types are differentiable based on differences in the length, width or shape of the particles and/or the number, composition, length or pattern of said segments. In other embodiments, the particles are differentiable based on the nature of their functionalization or physical properties (e.g., as measured by mass spectrometry or light scattering).

The present invention includes the manufacture of nanobar codes by the electrochemical deposition of metals inside a template wherein the process is improved, separately and collectively, by i) electroplating in an ultrasonication bath; and ii) controlling the temperature of the deposition environment, preferably by using a recirculating temperature bath.

Also included within the scope of the invention are methods for the simultaneous or parallel manufacture of a plurality of different types of nanobar codes. According to one such method, a plurality of templates are held in a common solution chamber and electrochemical deposition is accomplished by controlling deposition at each membrane by applying current selectively to predetermined electrodes associated with each such membrane.

Also included within this invention is an apparatus for the manufacture of nanobar codes comprising: a plating solution cell, a defined pore size template, means for applying a current to cause electrochemical deposition of a metal into said template, means for agitation of the plating solution, such as an ultrasonic transducer, and temperature control means.

Also included within this invention is an apparatus for the simultaneous manufacture of a plurality of different types of nanobar codes. In one embodiment, such apparatus comprises: a solution chamber, a plurality of templates, means for selectively applying a current to each of said templates, and control means for operating said apparatus.

DETAILED WRITTEN DESCRIPTION OF THE INVENTION

Figure 1:
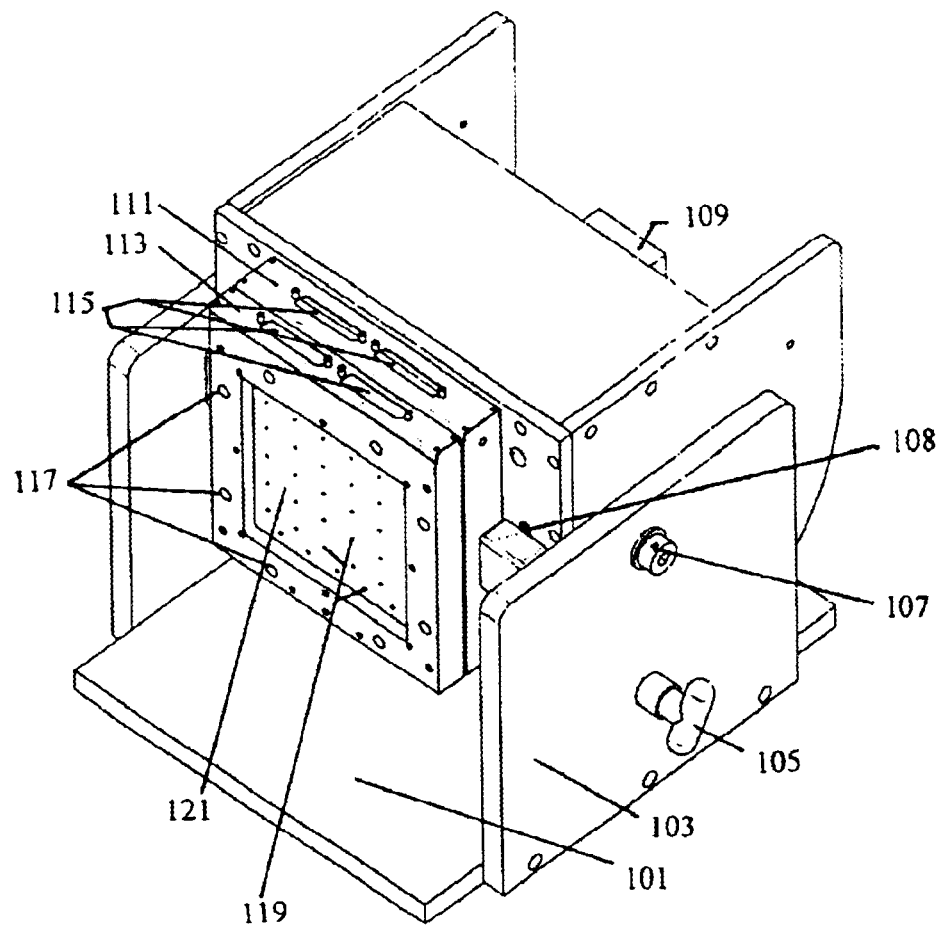
FIG. 1 is a perspective view of an apparatus for manufacturing a plurality of different types of nanobar codes.

The present application is directed to methods of manufacture of nanoparticles. Such nanoparticles and their uses are described in detail in U.S. Utility Application Ser. No. 09/598,395, filed Jun. 20, 2000, entitled "Colloidal Rod Particles as Nanobar Codes," incorporated hereby in its entirety by reference. Filed concurrently with the present application, and also incorporated herein in their entirety by reference, are two United States Utility Applications entitled "Methods of Imaging Colloidal Rod Particles as Nanobarcodes" and "Colloidal Rod Particles as Nanobar Codes." The present application is filed as a Continuation-in-Part of the 09/598,395 application.

The synthesis and characterization of multiple segmented particles is described in Martin et al., Adv. Materials 11: 10211–25 (1999). The article is incorporated herein by reference in its entirety. Also incorporated herein by reference in their entirety are U.S. Provisional Application Ser. No. 60/157,326, filed Oct. 1, 1999, entitled "Self Bar-coded Colloidal Metal Nanoparticles"; U.S. Provisional Application Ser. No. 60/189,151, filed Mar. 14, 2000, entitled "Nanoscale Barcodes"; U.S. Provisional Application Ser. No. 60/190,247, filed Mar. 17, 2000, entitled "Colloidal Rod Particles as Barcodes"; and U.S. Provisional Application Ser. No. 60/194,616, filed Apr. 5, 2000, entitled "Nanobarcodes: Technology Platform for Phenotyping."

Because bar coding is so widely-used in the macroscopic world, the concept has been translated to the molecular world in a variety of figurative manifestations. Thus, there are "bar codes" based on analysis of open reading frames, bar codes based on isotopic mass variations, bar codes based on strings of chemical or physical reporter beads, bar codes based on electrophoretic patterns of restriction-enzyme cleaved mRNA, bar-coded surfaces for repeatable imaging of biological molecules using scanning probe microscopies, and chromosomal bar codes (a.k.a. chromosome painting) produced by multi-chromophore fluorescence int situ hybridization. All these methods comprise ways to code biological information, but none offer the range of advantages of the bonafide bar codes of the present invention, transformed to the nanometer scale.

The particles to be manufactured according to the present invention are alternately referred to as nanoparticles, nanobar codes, rods, nanorods, nanobar codes, and rod shaped particles. To the extent that any of these descriptions may be considered as limiting the scope of the invention, the label applied should be ignored. For example, although in certain embodiments of the invention, the particle's composition contains informational content, this is not true for all embodiments of the invention. Likewise, although nanometer-sized particles fall within the scope of the invention, not all of the particles of the invention fall within such size range.

In preferred embodiments of the present invention, the nanobar code particles are manufactured by electrochemical deposition in an alumina or polycarbonate template, followed by template dissolution, and typically, they are prepared by alternating electrochemical reduction of metal ions, though they may easily be prepared by other means, both with or without a template material. Typically, the nanobar codes have widths between 30 nm and 1,000 nanometers, though they can have widths of several microns. Likewise, while the lengths (i.e. the long dimension) of the materials are typically on the order of 1 to 15 microns, they can easily be prepared in lengths as long as 50 microns, and in lengths as short as 20 nanometers. In some embodiments, the nanobar codes comprise two or more different materials alternated along the length, although in principle as many as dozens of different materials could be used. Likewise, the segments could consist of non-metallic material, including but not limited to polymers, oxides, sulfides, semiconductors, insulators, plastics, and even thin (i.e., monolayer) films of organic or inorganic species.

When the particles of the present invention are made by electrochemical deposition the length of the segments (as well as their density and porosity) can be adjusted by controlling the amount of current (or electrochemical potential) passed in each electroplating step; as a result, the rod resembles a "bar code" on the nanometer scale, with each segment length (and identity) programmable in advance. Other forms of deposition can also yield the same results. For example, deposition can be accomplished via electroless processes and in electrochemical deposition by controlling the area of the electrode, the heterogenous rate constant, the concentration of the plating material, and the potential and combinations thereof (collectively referred to herein as electrochemical deposition). The same result could be achieved using another method of manufacture in which the length or other attribute of the segments can be controlled. While the diameter of the rods and the segment lengths are typically of nanometer dimensions, the overall length is such that in preferred embodiments it can be visualized directly in an optical microscope, exploiting the differential reflectivity of the metal components.

The particles of this embodiment of the present invention are defined in part by their size and by the existence of at least 2 segments. The length of the particles can be from 10 nm up to 50 μm. In preferred embodiments the particle is 500 nm–30 μm in length. In the most preferred embodiments, the length of the particles of this invention is 1–15 μm. The width, or diameter, of the particles of the invention is within the range of 5 nm–50 μm. In preferred embodiments the width is 10 nm–1 μm, and in the most preferred embodiments the width or cross-sectional dimension is 30 nm–500 nm.

As discussed above, the particles of the present invention are characterized by the presence of at least two segments. A segment represents a region of the particle that is distinguishable, by any means, from adjacent regions of the particle. Segments of the particle bisect the length of the particle to form regions that have the same cross-section (generally) and width as the whole particle, while representing a portion of the length of the whole particle. In preferred embodiments of the invention, a segment is composed of different materials from its adjacent segments. However, not every segment needs to be distinguishable from all other segments of the particle. For example, a particle could be composed of 2 types of segments, e.g., gold and platinum, while having 10 or even 20 different segments, simply by alternating segments of gold and platinum. A particle of the present invention contains at least two segments, and as many as 50. The particles of the invention preferably have from 2–30 segments and most preferably from 3–20 segments. The particles may have from 2–10 different types of segments, preferably 2 to 5 different types of segments.

A segment of the particle of the present invention is defined by its being distinguishable from adjacent segments of the particle. The ability to distinguish between segments includes distinguishing by any physical or chemical means of interrogation, including but not limited to electromagnetic, magnetic, optical, spectrometric, spectroscopic and mechanical. In certain preferred embodiments of the invention, the method of interrogating between segments is optical (reflectivity).

Adjacent segments may even be of the same material, as long as they are distinguishable by some means. For example, different phases of the same elemental material, or enantiomers of organic polymer materials can make up adjacent segments. In addition, a rod comprised of a single material could be considered to fall within the scope of the invention if segments could be distinguished from others, for example, by functionalization on the surface, or having varying diameters. Also particles comprising organic polymer materials could have segments defined by the inclusion of dyes that would change the relative optical properties of the segments.

The composition of the particles of the present invention is best defined by describing the compositions of the segments that make up the particles. A particle may contain segments with extremely different compositions. For example, a single particle could be comprised of one segment that is a metal, and a segment that is an organic polymer material.

The segments of the present invention may be comprised of any material. In preferred embodiments of the present invention, the segments comprise a metal (e.g., silver, gold, copper, nickel, palladium, platinum, cobalt, rhodium, iridium); any metal chalcognide, a metal oxide (e.g., cupric oxide, titanium dioxide); a metal sulfide; a metal selenide; a metal telluride; a metal alloy; a metal nitride; a metal phosphide; a metal antimonide; a semiconductor; a semimetal. A segment may also be comprised of an organic mono- or bilayer such as a molecular film. For example, monolayers of organic moleculesor self assembled, controlled layers of molecules can be associated with a variety of metal surfaces.

A segment may be comprised of any organic compound or material, or inorganic compound or material or organic polymeric materials, including the large body of mono and copolymers known to those skilled in the art. Biological polymers, such as peptides, oligonucicotides and polysaccharides may also be the major components of a segment. Segments may be comprised of particulate materials, e.g., metals, metal oxide or organic particulate materials; or composite materials, e.g., metal in polyacrylamide, dye in polymeric material, porous metals. The segments of the particles of the present invention may be comprised of polymeric materials, crystalline or non-crystalline materials, amorphous materials or glasses.

Segments may be defined by notches on the surface of the particle, or by the presence of dents, divits, holes, vesicles, bubbles, pores or tunnels that may or may not contact the surface of the particle. Segments may also be defined by a discernable change in the angle, shape, or density of such physical attributes or in the contour of the surface. In embodiments of the invention where the particle is coated, for example with a polymer or glass, the segment may consist of a void between other materials.

The length of each segment may be from 10 nm to 50 μm. In preferred embodiments the length of each segment is 50 nm to 20 μm. The interface between segments, in certain embodiments, need not be perpendicular to the length of the particle or a smooth line of transition. In addition, in certain embodiments the composition of one segment may be blended into the composition of the adjacent segment. For example, between segments of gold and platinum, there may be a 5 nm to 5 μm region that is comprised of both gold and platinum. This type of transition is acceptable so long as the segments are distinguishable. For any given particle the segments may be of any length relative to the length of segments of the rest of the particle.

As described above, the particles of the present invention can have any cross-sectional shape. In preferred embodiments, the particles are generally straight along the lengthwise axis. However, in certain embodiments the particles may be curved or helical. The ends of the particles of the present invention may be flat, convex or concave. In addition, the ends may be spiked or pencil tipped. Sharp-tipped embodiments of the invention may be preferred when the particles are used in Raman spectroscopy applications or others in which energy field effects are important. The ends of any given particle may be the same or different. Similarly, the contour of the particle may be advantageously selected to contribute to the sensitivity or specificity of the assays (e.g., an undulating contour will be expected to enhance "quenching" of fluorophores located in the troughs).

In many embodiments of the invention, an assembly or collection of particles is prepared. In certain embodiments, the members of the assembly are identical, while in other embodiments, the assembly is comprised of a plurality of different types of particles. In embodiments of the invention comprising assemblies of identical particles, the length of substantially all of the particles for particles in the 1 μm–15 μm range may vary up to 50%. Segments of 10 nm in length will vary ±5 nm while segments in 1 μm range may vary up to 50%. The width of substantially all of the particles may vary between 10 and 100% preferably less than 50% and most preferably less than 10%.

The present invention includes assemblies or collections of nanobar codes made up of a plurality of particles that are differentiable from each other. Assembly or collection, as used herein, does not mean that the nanoparticles that make up such an assembly or collection are ordered or organized in any particular manner. Such an assembly is considered to be made up of a plurality of different types or "flavors" of particles. In some such assemblies, each of the nanobar codes of the assembly may be functionalized in some manner. In many applications, the functionalization is different and specific to the specific flavor of nanoparticle. The assemblies of the present invention can include from 2 to $10^{12}$ different and identifiable nanoparticles. Preferred assemblies include more than 10, more than 100, more than 1,000 and, in some cases, more than 10,000 different flavors of nanoparticles. The particles that make up the assemblies or collections of the present invention are segmented in most embodiments. However, in certain embodiments of the invention the particles of an assembly of particles do not necessarily contain a plurality of segments.

In certain embodiments of the invention, the particles of the present invention may include mono-molecular layers. Such mono-molecular layers may be found at the tips or ends of the particle, or between segments. Examples of the use of mono-molecular layers between segments are described in the section entitled ELECTRONIC DEVICES in U.S. Utility application Ser. No. 09/598,395, filed Jun. 20, 2000.

The present invention is directed to the manufacture of freestanding, nanobar codes. By "freestanding" it is meant that nanobar codes that are produced by some form of deposition or growth within a template have been released from the template. Such nanobar codes are typically freely dispensable in a liquid and not permanently associated with a stationary phase. Nanobar codes that are not produced by some foil of deposition or growth within a template (e.g., self-assembled nanobar codes) may be considered freestanding even though they have not been released from a template. The term "freestanding" does not imply that such nanoparticles must be in solution (although they may be) or that the nanobar codes can not be bound to, incorporated in, or a part of a macro structure. Indeed, certain embodiments of the invention, the nanoparticles may be dispersed in a solution, e.g. paint, or incorporated within a polymeric composition.

The particles of the present invention may be prepared by a variety of processes. The preferred process for the manufacture of a particular particle can often be a function of the nature of the segments comprising the particle. In most embodiments of the invention, a template or mold is utilized into which the materials that constitute the various segments are introduced. Defined pore materials are the preferred templates for many of the preferred particles of the present invention. $Al_2O_3$ membranes containing consistently sized pores are among the preferred templates, while photolithographically prepared templates, porous polycarbonate membranes, zeolites and block co-polymers may also be used. Methods for forming segments of particles include electrodeposition, chemical deposition, evaporation, chemical self assembly, solid phase manufacturing techniques and photolithography techniques. Chemical self assembly is a method of forming particles from preformed segments whereby the segments are derivatized and a chemical reaction between species on different segments create a juncture between segments. Chemically self-assembled nanoparticles have the unique ability of being controllably separated between segments by reversing the chemical bond formation process.

One of the preferred synthetic protocols used to prepare metallic nanobar codes according to the embodiments of the present invention is an extension of the work of Al-Mawlawi et al. (Al-Mawlawi, D.; Liu, C. Z.; Moskovits, M. *J Mater. Res.* 1994, 9, 1014; Martin, C. R. *Chem. Mater.* 1996, 8, 1739) on template-directed electrochemical synthesis. See, Example 1, below. In this approach, metals are deposited electrochemically inside a porous membrane. The synthetic method of the present invention differs from previous work in several respects including the following. First, the electroplating is done with agitation, such as in an ultrasonication bath. Second, the temperature is controlled, for example, by using a recirculating temperature bath. These first two modifications increase the reproducibility and monodispersity of rod samples by facilitating the mass transport of ions and gases through the pores of the membrane. Third, rods with multiple stripes are prepared by sequential electrochemical reduction of metal ions (e.g., $Pt^{2+}$, $Au^+$) within the pores of the membranes. Because the length of the segments can be adjusted by controlling the amount of current passed in each electroplating step, the rod resembles a "bar code" on the nanometer scale, with each segment length (and identity) programmable in advance. While the width of the rods and the segment lengths are generally of nanometer dimensions, the overall length is generally such that it can be visualized directly in an optical microscope, exploiting the differential reflectivity of the metal components.

There are many parameters in the nanorod synthesis that are tunable, such that it is theoretically possible to generate many millions of different patterns, uniquely identifiable by using conventional optical microscopy or other methods. The most important characteristic that can be changed is the composition of the striped rods. The simplest form of a nanoparticle is one with only one segment. To this end, several different types of these solid bar codes have been prepared. By simply using only one plating solution during the preparation, a solid nanoparticle is produced.

To generate two-segment nanobar codes, two metals (e.g., Au, Ag, Pd, Cu, etc.) can be electroplated sequentially, or simultaneously to form alloys. Nanobar codes can also be generated using 3 different metals. Synthesis of a Au—/Pt—/Au rod may be accomplished with 1 C of Au, 8 C Pt, and 1 C of Au. The nominal dimensions of the segments are 1 µm of Au, 3 µm of Pt, 1 µm of Au. The 5-segment nanobar codes, Ag—/Au—/Ag—/Au—/Ag, were generated by sequentially plating the appropriate metal. In some embodiments it is possible to include all metals in solution but control deposition by varying the charge potential current. A nine-segment nanobar code, Au—/Ag—/Au—/Ag—/Au—/Ag—/Au—/Ag—/Au has also been prepared. The number of segments can be altered to desired specifications.

The next controllable factor is diameter (sometimes referred to herein as width) of the individual rods. Many of the nanobar codes described were synthesized using membranes with a pore diameter of 200 nm. By altering the pore diameter, rods of differing diameter can be made. Au rods have been synthesized in a membrane that has 10 nm diameter pores, 40 nm pores and pores in the range of 200–300 nm.

The ends of the rods typically have rounded ends or flat ends. A TEM image of an Au rod that was made by reversing the current flow (from reduction at $-0.55$ mA/cm$^2$ to oxidation at $+0.55$ mA/cm$^2$) and removing some of the gold from the tip of the rod generated a spike extending from the tip of the rod. Additionally, branched ends can be generated. This can be typically controlled by controlling the amount of metal that is plated into the membrane. The edges of the membrane pores have a tendency to be branched which lead to this type of structure.

An additional way to alter the ends of the rods is to control the rate of deposition. Gold rods (2 C total, 3 µm) were plated at a current density of 0.55 mA/cm$^2$. Then the current density was reduced to 0.055 mA/cm$^2$ and 0.1 C of Au was plated. The last segment of gold deposits is a hollow tube along the walls of the membrane.

Example 1 describes the manufacture of single flavors of nanoparticles according to one embodiment of the invention.

In order to produce many thousands of flavors of nanorods, in practical quantities, and to attach molecules to most or all, novel combinatorial or multiplexed synthesis techniques are necessary. Several synthesis embodiments are included within the scope of the invention. Each approach has advantages and disadvantages depending on the specific application and the required number of types and total number of nanorods needed for the application.

The present invention includes methods of manufacture of nanoparticles that allow for the simultaneous or parallel manufacture of a plurality of different flavors of nanobar codes.

Prior to the present invention, no system or apparatus has been described whereby it was possible to prepare more than one type of nanobar code simultaneously or in parallel. In the preferred embodiments of this invention, such method for the simultaneous manufacture of nanobar codes allows for the manufacture of 2 or more, more than 5, more than the 10 and preferably more than 25 different flavors of nanobar codes. By simultaneous or parallel it is meant that common elements are employed in the manufacture of the more than one nanobar code. For example, in the apparatus depicted in FIGS. 1 and 2, there are 25 separate membranes, each with a separately controllable electrode connection on the back side, but with common access to the plating solution. In other embodiments, the separate membranes (or regions, on a single membrane) may have a common electrode, but separately controllable solution access. In still other embodiments, the simultaneous manufacture of different types of nanoparticles is commonly controlled. Any system or apparatus whereby a plurality of different flavors of nanoparticles (e.g, particles having a plurality of segments, that are 10 nm to 50 µm in length, and have a width from 5 nm to 50 µm that are differentiable from each other) can be prepared in parallel is included within the scope of this invention. Among the options that can be employed to affect this parallel manufacture are the following:

1. Multi-electrode and Microfluidic Synthesis: To synthesize many flavors of nanorods on a single membrane, the membrane can be divided into separate electrical zones, with each zone using a different plating recipe. Of course, several smaller membranes could be used, one for each separate zone, as opposed to a single membrane with multiple zones. The electrical zone approach can be achieved by patterning the Ag evaporation that initially seals one side of the membrane into many separate islands. Each island would have its own electrode, and control circuitry can activate each island separately for plating. The microfluidic approach utilizes a single evaporated Ag electrode, but would divide the opposite side of the membrane into separate fluidic regions, and control the flow of plating solutions to each region. Both of these techniques may be automated, and result in the synthesis of hundreds of nanorod flavors per membrane. Thousands to millions of flavors is probably not practical with either of these approaches due to practical limitations in the number of electrical or fluidic connections to the membrane 2. Patterned front-side insulation: This approach applies insulating patterned coatings (e.g., photoresist) to the front-side (electrodeposition side) of a membrane. Where the membrane is coated, electroplating is inhibited. The coating can be removed and reapplied with different pattern between electroplating steps to achieve synthesis of many flavors of nanobarcode within one membrane.

3. Patterned back-side insulation: This approach applies insulating patterned coatings (e.g., photoresist) to the back-side (electrode side) of a membrane, which is divided into many separate electrical contacts. Where the electrode is coated, electroplating is inhibited. The coating can be removed and reapplied with different patterns between electroplating steps to achieve synthesis of many flavors of nanobarcode within one membrane.

4. Lithography vertical or horizontal: This technique, that offers increased design flexibility in the size and shape of nanorods, utilizes lithographic processes to pattern the deposition of multiple layers of metals on a silicon substrate. This approach takes advantage of the tremendous capabilities developed in microelectronics and MEMS, and promises very high quality nanorods with greater design flexibility in the size and shape of nanorods than membrane-based techniques. Each of these synthetic approaches must be mated to complementary well arrays to allow nanobar release into separate vessels.

5. Light-addressable electroplating: A further technique that could produce thousands of flavors in one synthesis step also utilizes membrane-based synthesis, but includes light-directed control of the electroplating process. In this technique, a light-addressable semiconductor device is used to spatially modify the electrical potentials in the vicinity of the membrane, and thus spatially modulate electroplating currents. In this manner, the membrane is optically subdivided into many different zones, each of which produces a different flavor of nanorod.

6. Electrical multiplexing to multiple separate template membranes immersed in common plating solution: In this approach, multiple template membranes are immersed in a common plating solution, with a common anode electrode (platinum). Each membrane has a separate electrical connection from a computer-controlled current and/or voltage source to its silver-coated backside.

Several of these embodiments are based on existing procedures using defined-pore membranes. (i) One technique generates hundreds to perhaps a few thousand types of nanorods, by lithographically patterning the backside silver that is deposited on the membrane into isolated islands, each island forming an individually addressable electrical contact. By way of example, each island would have enough surface area to contain between $10^6$ and $10^8$ individual rods, all of the same type. (Note that since the membrane thickness, and therefore pore length, is much greater than the nanorod length, multiple nanorods can be synthesized in each pore. Each nanorod may be separated from others in the same pore by a silver plug that would later be dissolved. This could increase the total yield by 10×.) The membrane is then placed, with careful registration, onto a "bed-of-nails" apparatus, with individual spring-loaded pins contacting each electrode on the membrane. Computer-controlled circuitry attached to the bed-of-nails is able to individually turn on or off each electrode. During the electroplating process, each island would be plated with unique combinations of metal types and thicknesses. In this manner, each island would produce rods of different lengths, different numbers of stripes, and different material combinations, allowing ultimate design flexibility. (ii) The above approach will be limited in the number of types of rods that can be synthesized by the reliability and packing density of the bed-of-nails apparatus. To avoid this limitation, the bed-of-nails apparatus can be replaced by a liquid metal contact. To prevent the liquid bath from simultaneously contacting every electrode, the backside of the membrane may be patterned with a nonconductive coating. To individually address electrodes during synthesis, the pattern would be removed and replaced with a different pattern between electroplating steps. This approach will enable a much higher density of isolated islands, and therefore more types of rods to be synthesized. With island spacing of 100 microns, which would be trivial to achieve using lithographical patterning, up to $10^5$ types of rods could be synthesized. Since the total number of pores in each membrane is a constant there will be proportionally fewer rods of each type. (iii) The above two approaches use commercially available aluminum oxide membrane filters, which have pore size and density that are suitable for nanorod synthesis. However, the membrane thickness is typically greater than that required, which can cause variability in rod and stripe lengths due to non-uniform mass transport into the pores during electroplating. Also, the largest pores available in these membranes (and thus nanorod widths) are 250 nm, and it would be desirable for some applications to have rod widths of 1 micron or more (this could also be used for embodiment with widths of less than 1 µm).

To address these issues, pore matrices may be constructed using photolithography techniques, which will give ultimate control over the pore dimensions and lengths, and increase the design flexibility and quality of the resulting nanorods. According to this embodiment a positive photoresist-coated wafer is exposed to an interference pattern of light, using a technique similar to that used for interference-lithography generated diffraction gratings. The wafer is typically silicon, with a thin coating of titanium and gold, a thick coating of polymethylmethacrylate (PMMA), and a photoresist. Two exposures at right angles and subsequent development yields a two-dimensional array of holes in the photoresist. Reactive ion etching is then used to transfer the hole pattern down through the PMMA layer, which becomes the template. The photoresist layer is removed, and the gold layer under the PMMA becomes the cathods for electroplating into the PMMA pores. The shape and diameter of the nanorods can be controlled by adjusting the light source and the resultant standing wave pattern.

An advantage to this technique is that the template thickness, which is the same as pore length, can be tailored to the length of the rods, which improves uniformity of electroplating across the membrane. With this technique, $10^{10}$ to $10^{12}$ nanorods can be constructed on a single substrate. The two approaches described above can be utilized to synthesize many types of nanobar code from a single wafer. (iv) A further approach uses the customized lithographically-defined pores from above, and achieves the ultimate in design flexibility by using novel light-directed electroplating. The template pores are constructed just as in the third approach, but on top of a photosensitive semiconductor wafer. The pore-side of the wafer is immersed in electroplating reagent, and the other side is illuminated with patterns of light. Light exposure is used to generate photocurrent in the wafer, and switch the plating current on or off for each conductive zone within the wafer. A computer-controlled spatial light modulator selectively illuminates different zones at different times, so that each zone will be subjected to a different computer-controlled plating recipe. Depending on the resolution of the optical system that exposes the wafer, this could result in $10^4$ to $10^6$ separate flavors of nanorods synthesized on a single wafer. With $10^{12}$ total pores per wafer, $10^6$ to $10^8$ nanorods of each flavor could be synthesized.

It should be noted that there are numerous other materials that can be used to prepare membranes or templates for nanorod synthesis. One example of many are bundles of optical fibers in which the cores are etchable under conditions where the claddings are not. Carrying out this etching, followed by slicing across the bundle, yields a membrane with hole diameters the size of the fiber cores. Note that fibers can be drawn out (using heat) to submicron diameters. Note also that fiber bundles with collections of greater than 1,000,000 fibers are commercially available; this could easily be extended to 10 million. Another group of materials that could be used, for example, are molecular sieve materials with well-defined cavities such as zeolites.

Note also that other methods can be used to prepare templates or membranes from a variety of different methods. Such methods include but are not limited to: MEMS, electron beam lithography, x-ray lithography, uv lithography, deep lithography, projection lithography, standing wave lithography, interference lithography, and microcontact printing.

Chemical self-assembly/deassembly methods may also be used. For example, formation of an infinite, close-packed, 2-dimensional hexagonal layer of latex balls on a planar surface has been demonstrated. Such particles could be shrunk by 10% in size, e.g., by cooling the temperature. Then a polymer may be grown in the spaces between the infinite 2-D array (that is no longer close packed). Then the balls are selectively dissolved, leaving behind a polymeric material with well defined holes equal to the final diameter of the latex balls.

The particles of the present invention may also be prepared in large scale by automating the basic electroplating process that is described in Example 1. For example, an apparatus containing a series of membranes and separate electrodes can be used to make a large number of different flavors of nanoparticles in an efficient computer controlled manner. An example of this type of apparatus is depicted in FIGS. 1 and 2.

Figure 2:
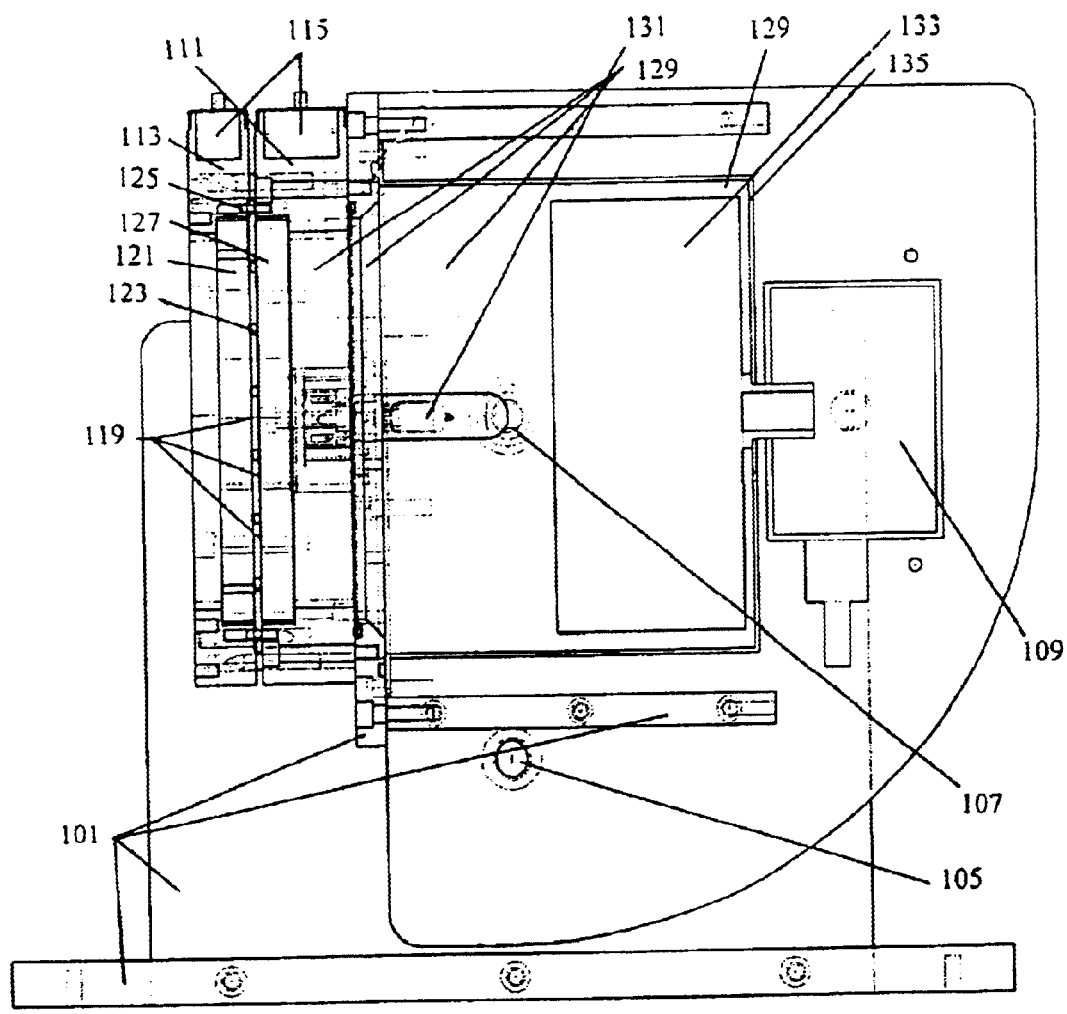
FIG. 2 is a cross-sectional elevation view of the apparatus of FIG. 1.

The embodiment of the invention depicted in FIGS. 1 and 2 synthesizes 25 types of nanobar codes simultaneously in 25 separate template membranes (e.g., Whatman Anodisc membranes, 25 mm diameter, 60 micron thick, with 200 nm pores) mounted in a liquid flow cell. Before mounting the membranes in the flow cell, each membrane is silver-coated on one side (which is the branched-pore side of the membrane) in a vacuum evaporator. Then each membrane is immersed in a silver plating solution with electrodes on both sides, and additional silver is electroplated onto the evaporated silver coating and into the pores (at 4 mA for about 30 minutes), to completely close all of the membrane pores.

Each membrane is then mounted with its silver-coated side in contact with an electrode in the flow cell. The flow cell is about 1.5 mm thick, containing about 30 ml of liquid. Opposite the membranes is a platinum mesh electrode with surface area slightly larger than the entire 5×5 array of membranes.

The flow cell can be filled (by computer control) with water, nitrogen gas, gold plating solution (e.g., Technics), silver plating solution (e.g.,Technics Silver Streak and/or additional plating solutions). The flow cell is in thermal contact with a coolant water tank, the temperature of which is controlled by recirculation through a temperature-controlled bath. In the coolant tank opposite the flow cell is an ultrasonic transducer (Crest, 250 Watt), which is turned on during electroplating operations to facilitate mass transport of ions and gases through the membrane pores. Control software is used to automatically flow the appropriate solutions through the flow cell, and individually control the electroplating currents or potentials at each separate membrane. The software also measures temperature at various locations in the apparatus, and controls the sonicator and peristaltic pump. The software allows the user to define recipes describing the desired stripe pattern for each nanobar code in the 5×5 array. The software reads the recipe, and then automatically executes all fluidic and electrical steps to synthesize different types of nanobar codes in each membrane.

After nanorod synthesis is complete, the membranes are removed from the flow cell, and individually postprocessed to free the nanobar codes from the template pores. First, each membrane is immersed in approximately 2M HN (nitric acid) for about 30 minutes to dissolve the backside silver coating. Then the membrane is immersed in NaOH to dissolve the alumina membrane, and release the rods into solution. The rods are then allowed to settle under gravity, and the NaOH is washed out and replaced with $H_2O$ or Ethanol for storage. In a further embodiment, rather than moving the solution exposed to a stationary membrane or template, moving the membranes or templates may be moved from one plating solution to another.

An apparatus for performing such manufacture of 25 types or flavors of nanobar codes is depicted in FIGS. 1 and 2. As described above, 25 separate membrane templates are placed in a common solution environment, and deposition is controlled by the application of current to the individual membranes. For example, membranes 1–10 may begin with the deposition of a layer of gold that is 50 nm thick, membranes 11–20 may begin with the deposition of gold that is 100 nm thick, while membranes 21–25 may not have an initial layer of gold. This deposition step can be easily accomplished in the apparatus of this embodiment by filling the solution reservoir with a gold plating solution and applying current to membranes 1–10 for the predetermined length of time, membranes 11–20 for twice as long and not at all to membranes 21–25. The gold plating solution is then removed from the chamber and the chamber rinsed before introducing the next plating solution.

The apparatus of this embodiment has been designed to be rotatable around a pivot point for ease of access to the solution chamber and the electric and plumbing controls on the back of the apparatus. Referring to FIG. 1, the apparatus rests upon a base 101. The pivoting mechanism is comprised of the pivoting support 103, the pivot locking pin handle 105, and the pivot pin 107. The apparatus is equipped with a halogen light, contained in the box 108, and a sonicator, located at 109, in fluid communication with a solution chamber.

The flow cell is defined by the rear cell assembly 111 and the front cell assembly 113. The electrical connectors 115 are on the tops of the rear and front assemblies. The assemblies are held in place by clamping bolts 117 to maintain a sealed solution chamber. The 25 templates 119 for nanoparticle growth are held between front and rear assemblies, and the front assembly has an electroforming cell front window 121.

FIG. 2 is a cross-sectional view of the apparatus shown in FIG. 1. Many of the same elements can be seen in FIG. 2 that were defined with respect to FIG. 1, and they have been numbered the same. FIG. 2 also allows visualization of cell partitioning gaskets 123 between front and rear assemblies and gasket alignment pin 125. FIG. 2 also shows rear assembly glass window 127. The water tank 129 for temperature control is found adjacent to the rear assembly, and the halogen lamp 131 is shown. The ultrasonic apparatus is comprised of the ultrasonic transducer 133 and the ultrasonic tank 135.

While the embodiment described above clearly illustrates how twenty-five types of nanobar codes comprising cylindrical, segmented metal nanoparticles can be prepared by parallel synthesis, the concept has very broad applicability. It is straightforward to extend this embodiment to hundreds or thousands of parallel reaction chambers. Likewise, it is straightforward to extend this method to the fabrication of nanorods with three or more different materials. Likewise, it should be clear that, through appropriate use of Ag spacers, that more than one flavor of nanobar code can be prepared within a single reaction vessel. In other words, one could prepare an Au—Pt rod, deposit Ag, and then prepare an Au—Pt—Au rod. After rod release from the membrane, Ag dissolution will lead to production of two types of rods. Of course, the number of a single type of particles could be increased by growing multiple copies of a single rod within the same reaction vessel.

It should likewise be realized that, rather than introduction of one plating solution to a collection of membranes, it is straightforward to employ microfluidics to address templates individually. In other words, a different plating solution could simultaneously be delivered to two or more locations. Thus, in principle, one could be making stripes of 5 or 10 or more compositions, and with 5 or 10 or more segment widths, at the same time, but in different, pre-programmed locations.

Importantly, the materials chosen for this synthesis (Au, Ag, Pt) are meant to be illustrative, and in no way limiting. There are numerous materials that can be electrodeposition in this fashion, including metals, metal oxides, polymers, and so forth, that are amenable to multiplexed synthesis.

More generally, multiplexed synthesis of nanoparticles need not be confined to electrochemical deposition into a host. For example, the materials described herein could likewise be prepared by sequential evaporation, or by sequential chemical reaction. This expands the possibilities for multiplexed nanoparticle synthesis to include all oxides, semiconductors, and metals.

Independent of the synthetic approach used, when synthesis is done in a membrane a final critical step is required to separate each unique type of nanorod and release all the nanorods into solution, for surface preparation or denaturation. In the preferred embodiments of the invention this is done by chemical dissolution of the membrane and electrode backing, using a series of solvents. These solvents could be acids, bases, organic or aqueous solutions, at one or more temperature or pressures, with one or more treatment times. Two additional release techniques are: (i) Following synthesis, whether on membrane or planar substrate, die separation techniques from the semiconductor industry can be utilized. The substrate will be mated to a flexible adhesive material. A dicing saw cuts through the substrate, leaving the adhesive intact. The adhesive is then uniformly stretched to provide physical separation between each island, each of which is then picked up automatically by robot and placed into a separate microwell. An automated fluidics station is used to introduce the necessary etching solutions to release each rod into solution. (ii) An alternative embodiment is a matching microwell substrate that contains wells in the same pattern as the individual islands in the membrane, and a matching array of channels through which flow etching solutions. The membrane or wafer can be sandwiched between the microwell substrate and the channel array. Etching fluid is then introduced into the channels which dissolves the Ag backing and carries the nanorods into the corresponding well. Other means for removing the particles from the membrane are also possible, including but not limited to laser ablation, heating, cooling, and other physical methods.

The membrane-based template-directed synthesis techniques are preferred because they are capable of making a very large number of very small nanorods. The electroplating conditions can be adequately controlled to produce many types of nanorod bar codes. For applications such as multiplexed immunoassays, where tens to many hundreds of types are required, known techniques are adequate and can simply be scaled up to provide the necessary number. For applications such as proteomic signatures, where from dozens to many thousands of types are required, higher throughput synthesis techniques and the ability to uniquely identify each of thousands of different bar codes are required.

EXAMPLES

The following examples are provided to allow those skilled in the art access to information regarding various embodiments of the present invention, and are not intended in any way to limit the scope of the invention.

Example 1

One embodiment of the present invention is directed to the template-directed synthesis of multiple flavors of nanobar codes for the purpose of multiplexed assays. For this application it is desirable to construct a variety of different flavors which are easily distinguished by optical microscopy. For example, 10 different flavors of nanobar codes were individually synthesized according to the table below, using gold and silver segments. Note that the description field of the table indicates the composition of each nanobar code by segment material and length (in microns) in parentheses. For example, Flavor #1 is 4 microns long gold, and Flavor #2 is 2 microns gold followed by 1 micron silver, followed by 2 microns gold.

| Flavor # | Description | # Segments | Length |
| --- | --- | --- | --- |
| 1 | Au(4) | 1 | 4 µm |
| 2 | Au(2), Ag(1), Au(2) | 3 | 5 µm |
| 3 | Au(1), Ag(1), Au(1), Ag(1), Au(1) | 5 | 5 µm |
| 4 | Au(2), Ag(2) | 2 | 4 µm |
| 5 | Ag(1), Au(1), Ag(1), Au(1), Ag(1) | 5 | 5 µm |
| 6 | Ag(1), Au(4) | 2 | 5 µm |

-continued

| Flavor # | Description | # Segments | Length |
|---|---|---|---|
| 7 | Ag(4) | 1 | 4 μm |
| 8 | Ag(1), Au(2), Ag(1) | 3 | 4 μm |
| 9 | Ag(1), Au(1), Ag(1), Au(2) | 4 | 5 μm |
| 10 | Ag(2), Au(1), Ag(1), Au(1) | 4 | 5 μm |

A detailed description of the synthesis of Flavor #4 follows. (All other flavors were synthesized by minor and obvious changes to this protocol.)

25 mm diameter Whatman Anopore disks with 200) nm diameter pores were used for template directed nanobar code synthesis. Electrochemical metal deposition was carried out using commercially available gold (Technic Orotemp 24), and silver (Technic ACR 1025 SilverStreak Bath) plating solutions. All of the electroplating steps described below were carried out in an electrochemical cell immersed in a sonication bath, which was temperature controlled to 25° C.

The synthesis of nanobar code Flavor #4 was carried out as follows. The membrane was pretreated by evaporating ~500 nm of silver on its branched side. To completely fill the pores on this side, approximately 1 C of silver was electroplated onto the evaporated silver, using 1.7 mA of plating current for approximately 15 minutes. Then an additional 1 C of silver was electroplated into the pores of the membrane from the side opposite the evaporated silver, using 1.7 mA of plating current for approximately 15 minutes. This silver layer is used to fill up the several micron thick "branched-pore" region of the membrane. The silver plating solution was removed by serial dilutions with water, and was replaced by the gold plating solution. The 2 micron long gold segments were then deposited using 1.7 mA of plating current for approximately 30 minutes. The gold plating solution was removed by serial dilution with water, and was replaced by the silver plating solution. The final 2 micron long silver segment was then deposited using 1.7 mA of plating current for approximately 30 minutes. The membrane was removed from the apparatus, and the evaporated silver layer (and the electrodeposited silver in the branched pores) was removed by dissolution in 6 M nitric acid, being careful to expose only the branched-pore side of the membrane to the acid. After this step, the nanobar codes were released from the alumina membrane by dissolving the membrane in 0.5 M NaOH. The resulting suspension of nanobar codes were then repeatedly centrifuged and washed with water.

Example 2

It is an important goal to demonstrate the ability to use a wide number of materials in the nanobar codes of the present invention. To date, rod structures formed by electrochemical deposition into a membrane template (alumina or track etch polycarbonate) include Ag, Au, Pt, Pd, Cu, Ni, CdSe, and Co. Primarily, the 200-nm pore diameter alumina membranes have been used for convenience. Many of the materials are now also being used in the smaller diameter polycarbonate membranes.

CdSe is currently plated via a potential sweep method from a solution of $CdSO_4$ and $SeO_2$. Mechanical stability problems have been encountered with the metal:CdSe interface; i.e. they break when sonicated during the process of removing them from the membrane. This has been remedied with the addition of a 1,6-hexanedithiol layer between each surface.

The Cu and Ni are plated using a commercially available plating solution. By running under similar conditions as the Ag and Au solutions, it was found that these metals plate at roughly the same rate, ~3 μm/hr. The Co is plated from a $CoSO_4$/Citrate solution. These rods seems to grow fairly monodispersely, however they grow comparatively slowly, ~1.5 μm/hr.

Example 3

One embodiment of the present invention is directed to the template-directed synthesis of nanoscale electronic devices, in particular diodes. One approach, combines the membrane replication electrochemical plating of rod-shaped metal electrodes with the electroless layer-by-layer self-assembly of nanoparticle semiconductor/polymer films sandwiched between the electrodes. Described below, is the wet layer-by-layer self-assembly of multilayer $TiO_2$/polyaniline film on the top of a metal nanorod inside 200 nm pores of an alumina membrane.

1. Materials 200 nm pore diameter Whatman Anoporedisks ($Al_2O_3$-membranes) were used for template directed diode synthesis. Electrochemical metal deposition was carried out using commercially available gold (Technic Orotemp 24), platinum (Technic TP), and silver plating solutions. Titanium tetraisopropoxide[Ti(ipro)$_4$], mercaptoethylamine hydrochloride(MEA),ethyltriethoxy silane, chlorotrimethyl silane were purchased from Aldrich. All the reagents were used without further purification. All other chemicals were reagent grade and obtained from commercial sources.

$TiO_2$ colloid was prepared as follows. Ti(ipro)$_4$ was dissolved in 2-methoxyethanol under cooling and stirring. The solution was kept under stirring until it became slightly yellow, after which another portion of 2-methoxyethanol containing HCl was added. The molar ratio of the components in the prepared solution was Ti(ipro)$_4$: HCl:2-metoxyethanol=1:0.2:20. This solution was diluted with water to adjust $TiO_2$ concentration to 1% and allowed to age during 3 weeks. The resulting opalescent sol was subjected to the rotary evaporation at 60° C. to give shiny powder of xerogel containing 75% (w/w) titania. This xerogel was used as a precursor for the preparation of stock aqueous $TiO_2$ sol with $TiO_2$ concentration of 2.3% wt (0.29 M) and pH=3, which was stable during several weeks. XRD investigations of the titania xerogel allowed estimating average size of the colloidal anatase crystals at 6 nm, TEM image of the stock $TiO_2$ sol shows particles of 4–13 nm in diameter.

The emmeraldine base (EB) form of polyaniline (PAN) was also prepared. A dark blue solution of PAN in dimethyl formamide (0.006% wt) was used as a stock solution for the film synthesis.

2. Synthesis of Rod-shaped Diodes

The synthesis of rod-shaped diodes was carried out as follows. Metal electrodes were grown electrochemically inside porous membrane. Briefly, the membrane was pretreated by evaporating ~150 nm of silver on its branched side. To completely fill the pores on this side 1 C of silver was electroplated onto the evaporated silver. These Ag "plugs" were used as foundations onto which a bottom electrode was electrochemically grown. The bottom gold electrode of desired length was electroplated sonicating. The plating solution was removed by soaking the membrane in water and drying in Ar stream. Priming the bottom electrode surface with MEA preceded depositing multilayer $TiO_2$/PAN film. This was achieved by 24 hour adsorption from MEA(5%) ethanolic solution. The multilayer film was grown by repeating successive immersing the membrane in the $TiO_2$ aqueous solution and PAN solution in DMF for 1 h. Each adsorption step was followed by removing the excess of reagents by soaking the membrane in several portions of an appropriate solvent (0.01 M aqueous HCl or DMF) for 1 h, and drying in Ar stream. Finally, a top electrode (Ag or Pt) of desired length was electroplated at the top of $TiO_2$/PAN multilayer without sonicating. Then the evaporated silver, "plugs" and alumina membrane were removed by dissolving in 6 M nitric acid and 0.5M NaOH, respectively. (2–4 C of Au was always electroplated on the top of Ag electrode to prevent dissolving the latter in the nitric acid. Also preliminary experiments showed that multilayer $TiO_2$/PAN film self-assembled on plane Au(MEA) substrate did not destroy in the 0.5 M NaOH.) The resulting rod-shaped diodes were repeatedly centrifuged and washed with water.

In most of the experiments, chemical passivation of $Al_2O_3$-membrane pore walls was applied using treatments with propionic acid or alkylsilane derivatives. In the latter case, a membrane was successively soaked in absolute ethanol and anhydrous toluene or dichlorethane for 1 h, after which it was immersed in a ethyltriethoxy silane solution in anhydrous toluene (2.5% vol) or a chlorotrimethyl silane solution in anhydrous dichlorethane (2.5% vol) for 15 h. Then the membrane was successively soaked for 1 h in the appropriate anhydrous solvent, a mixture (1:1) of the solvent and absolute ethanol, the absolute ethanol, and finally was dried in Ar stream. Wetting so treated membranes with water revealed hydrophobic properties of their external surface. Transmission IR spectra of the membrane treated with ethyltriethoxy silane or propionic acid showed the appearance of weak bands at 2940, 2865, 2800 cm-1, which can be assigned to C—H stretching vibrations of alkyl and alkoxy groups.

3. Characterization

Transmission electron microscope (TEM) images were obtained with a JEOL 1200 EXII at 120 kV of accelerating voltage and 80 mA of filament current.

Optical microscope (OM)images were recorded. Transmission IR spectra were recorded using a Specord M-80 CareZeiss Jena spectrometer. I—V characteristics for rod-shaped diodes were measured in air at ambient temperature.

TEM images of some typical "striped" bimetallic Au/Pt/Au nanorods, grown electrochemically inside the porous alumina membrane showed that the two rod ends differed in their topography—one of the rod ends appeared to be bulging or rounded while the other rod end had an apparent hollow in the middle. Such differences in rod end appearance could be explained by adsorption of some amount of metal ions on pore walls, promoting metal (e.g. Ag) growth in the near-wall space and causing the hollow formation in the pore middle space. During the electroplating of a second metal "stripe" (e.g. Au), the growing metal follows the surface of the bottom rod and fills the hollow thus forming the rounded end. Further rod growth results in a cup-like end due to the metal adsorption on the pore walls. Each sequential metal segment grows in the same way in the end of the underlying segment.

It is unlikely that the relatively rough surface on the top end of a rod may be completely covered with the ultrathin $TiO_2$/PAN film thus preventing immediate contacts between bottom and top metal electrodes. From preliminary experiments on plane Au-substrates, it was found that the multilayer $TiO_2$/PAN films grown on smoother surfaces demonstrated better reproducibility in their rectifying behavior. Passivation (hydrophobization) of $Al_2O_3$-terminated surface of pore walls with propionic acid or alkylsilane derivatives, such as ethyltriethoxy silane or chlorotrimethyl silane, was tried to smooth down the top rod end surface by reducing the metal adsorption on the pore walls. The hydrophobization of pore walls may also be expected to prevent $TiO_2$ particles from adsorption on the wall surface rather than on metal electrode surface situated in the depth (~65 mm) of the pore. It was shown that the $TiO_2$ particles readily formed a densely packed layer on a plane Al/$Al_2O_3$ substrate. A typical higher resolution image of rod's upper part confirmed that the cup-like ends are situated at the top of the rods, and showed that the wall passivation to some extent resulted in smoothing of the surface of rod ends.

An optical micrograph of Au/($TiO_2$/PAN)$_{10}$/Ag/Au rods, prepared using the membrane derivatized with ethyltriethoxy silane, showed nanorods of uniform length, in which a silver segment is clearly seen between two gold ends. TEM images of such a rod, recorded in the first several seconds, revealed no visible signs of a metal/film/metal heterojunction within the rod. However, after focusing the electron beam on this rod for some time (typically tens of seconds), a break appeared in the rod and metal segments became separated, perhaps due to beam-induced metal melting, in the neighborhood of the Au/film/Ag heterojunction. In higher resolution TEM images of this break, particles of 5–10 nm in diameter, which adhere to both metal ends, were observed. Apparently, $TiO_2$ nanoparticles are present between two electroplated metals. The OM and TEM data suggest that the self-assembly of multilayer $TiO_2$/PAN film on the Au rod top can be realized inside the membrane pores, and that the self-assembled film does not prevent Ag rod electroplating on the top of the film. It should be noted that TEM images in all likelihood do not give a true picture of the multilayer $TiO_2$/PAN film inside the rod because of high probability of the mechanical film destruction while separating partially melted metal rod ends. Longer time exposure of the rod to the electron beam causes complete destruction of the heterojunction and arising two individual nanorods with nanoparticles stuck to their ends.

In order to investigate multilayer $TiO_2$/PAN film sandwiched between Au and Ag rods, Au|($TiO_2$/PAN)$_6$/Ag nanorods were prepared and their top Ag electrode was dissolved in nitric acid. The remaining 2C Au rods with ($TiO_2$/PAN)$_6$ film deposited on their top were analyzed by TEM. Preliminary studies showed that ellipsometric thickness of multilayer $TiO_2$/PAN film self-assembled on plane Au(MEA) substrate did not decrease after immersion in 6 M $HNO_3$ for 30 mm suggesting stability of the film in the acidic medium. Furthermore, similar to the Au/($TiO_2$/PAN)$_{10}$/Ag/Au rods described above, TEM image of the Au/($TiO_2$/PAN)$_6$ rod taken in the first several seconds did not reveal any particles. However, during longer exposure to the electron beam, gold melted revealing nanoparticle film on the rod's top. It can be seen that the upper contour line of the film is very close to that of Au rod before melting. This fact is consistent with the cup-shaped top of the metal rods. The multilayer film grows on the surface both of cup bottom and cup walls and approximately retains cup shape after the thin walls have melted. This explanation is consistent with observed film height of ~100 nm, which allows estimating rather gold cup depth than ($TiO_2$/PAN)$_6$ film thickness. Ellipsometric thickness of $TiO_2$/PAN)$_6$ film self-assembled on a plane Au(MEA) substrate is estimated at about 10 nm.

I—V characteristic of the Pt/($TiO_2$/PAN)$_3$ $TiO_2$/Au rod-shaped device reveals current rectifying behavior. The forward and reverse bias turn-on potentials are –0.2 and ~0.9 V, respectively.

We claim:

1. A method for the manufacture of a freestanding segmented nanoparticle by the deposition of a plurality of materials inside a template, comprising:
   a) causing deposition of a first material into a pore of said template;
   b) causing deposition of a second material into said pore of said template, wherein the deposition of at least one of said first material and said second material is electrochemical deposition; and
   c) releasing said segmented nanoparticle from said template to provide a freestanding segmented nanoparticle having a length from 10 nm to 50 μm and a width from 5 nm to 50 μm, wherein said freestanding segmented nanoparticle comprises 50 or fewer segments.

2. The method of claim 1 wherein said segmented nanoparticle has a length from 1–15 μm and a width from 30 nm to 2 μm.

3. The method of claim 1 wherein said first and second materials are selected from the group consisting of a metal, a metal chalcogenide, a metal oxide, a metal sulfide, a metal selenide, a metal telluride, a metal alloy, a metal nitride, a metal phosphide, a metal antimonide, a semiconductor, a semi-metal, an organic compound or material, a inorganic compound or material, a particulate layer of material and a composite material.

4. The method of claim 1 wherein said first or second material is a metal.

5. The method of claim 4 wherein said metal is selected from the group consisting of silver, gold, copper, nickel, palladium, platinum, cobalt, rhodium, and iridium.

6. The method of claim 1 wherein said template is selected from the group consisting of an $Al_2O_3$ membrane, a photolithographically prepared template, a porous polycarbonate membrane, a zeolite and a block copolymer.

7. The method of claim 1 wherein an electrode is placed on or in proximity to one surface of said template, and said template is placed in contact with a first plating solution to deposit said first material, and is placed in contact with a second plating solution to deposit said second material.

8. The method of claim 1 wherein said segmented nanoparticles has a width of at least 500 nm.

9. The method of claim 1 wherein said segmented nanoparticle has a width of at least 1 μm.

10. The method of claim 1 wherein said segmented nanoparticle has a width of at least 2 μm.

11. The method of claim 1 wherein at least one of said segments has a length of at least 10 nm.

12. The method of claim 1 wherein at least one of said segments has a length of at least 50 nm.

13. The method of claim 1 wherein said plurality of materials comprises at least 3 materials.

14. The method of claim 1 wherein said plurality of materials comprises at least 4 materials.

15. The method of claim 1 wherein said plurality of materials comprises at least 5 materials.

16. A method for the manufacture of a freestanding segmented nanoparticle by the deposition of a plurality of materials inside a template, comprising:
   a) causing deposition of a first material into a pore of said template;
   b) causing deposition of a second material into said pore of said template, wherein the deposition of at least one of said first material and said second material is electrochemical deposition; and
   c) releasing said segmented nanoparticle from said template to provide a freestanding segmented nanoparticle having a length from 10 nm to 50 μm and a width from 5 nm to 50 μm, wherein at least one of said segments has a length of at least 10 nm.

17. The method of claim 16 wherein said segmented nanoparticle has a length from 1–15 μm and a width from 30 nm to 2 μm.

18. The method of claim 16 wherein said segmented nanoparticle has a width of at least 500 nm.

19. The method of claim 16 wherein said segmented nanoparticle has a width of at least 1 μm.

20. The method of claim 16 wherein said segmented nanoparticle has a width of at least 2 μm.

21. The method of claim 16 wherein said freestanding segmented nanoparticle comprises about 50 or fewer segments.

22. The method of claim 16 wherein at least one of said segments has a length of at least 50 nm.

23. The method of claim 16 wherein said plurality of materials comprises at least 3 materials.

24. The method of claim 16 wherein said plurality of materials comprises at least 4 materials.

25. The method of claim 16 wherein said plurality of materials comprises at least 5 materials.

* * * * *